United States Patent [19]

Bradley et al.

[11] Patent Number: 4,622,457
[45] Date of Patent: Nov. 11, 1986

[54] AUTOSAMPLER MECHANISM

[75] Inventors: Martin P. T. Bradley, Cupertino; Leslie A. Miller, San Jose; Thomas J. McCall, Fremont; Duane L. Middlebusher, San Jose, John H. Henselman, Pleasanton, all of Calif.

[73] Assignee: Spectra-Physics, Inc., San Jose, Calif.

[21] Appl. No.: 627,442

[22] Filed: Jul. 3, 1984

Related U.S. Application Data

[62] Division of Ser. No. 241,810, Mar. 9, 1981, Pat. No. 4,478,099.

[51] Int. Cl.$^4$ .............................................. G06K 7/10
[52] U.S. Cl. .................................. 235/464; 235/375; 235/462
[58] Field of Search ..................... 235/462, 464, 375; 250/566

[56] References Cited

U.S. PATENT DOCUMENTS

| | | | |
|---|---|---|---|
| 3,663,801 | 5/1972 | Wahli | 250/566 |
| 3,673,417 | 6/1972 | Wahli | 250/566 |
| 3,848,112 | 11/1974 | Weichselbaum | 235/375 |
| 4,164,320 | 8/1979 | Irazoqui | 235/375 |

Primary Examiner—Harold I. Pitts
Attorney, Agent, or Firm—Donald C. Feix

[57] ABSTRACT

A sampler for taking samples from multiple sources has a fixed, non-moving needle at a sampling station. A sample vial is lifted from a tray at the sampling station. The needle pierces the septum of the vial and enters the sample as the vial is lifted toward the needle.

The sample vial is also rotated as it is lifted, and a bar code reader makes a number of spaced apart, helical reads on a bar code label attached to the vial for label identification of the sample.

The needle includes an inner, sample needle and an outer, gas-pressurization needle. The sample is withdrawn by the positive displacement of a syringe connected to the sample needle. The combination of the gas pressurization within the vial and the positive displacement of the syringe insures movement of the sample and accurate control of the volume removed independent of the viscosity of the sample.

The vial tray mechanism for carrying the sample vials to and from the sample station includes a rotatable platter and four planetary trays carried by and rotatable on the platter. A clutch and brake drive permits the entire tray assembly to be rotated as a unit and also permits rotation of the planetary trays relative to the main platter so that any sample vial can be positioned at the sample station in any desired sequence with respect to the other sample vials.

2 Claims, 8 Drawing Figures

AUTOSAMPLER MECHANISM

This is a divisional of co-pending application Ser. No. 06/241,810 filed on Mar. 9, 1981 now U.S. Pat. No. 4,478,099 issued Oct. 23, 1984.

BACKGROUND OF THE INVENTION

This invention relates to apparatus and methods for taking samples from multiple sources. It has particular application to an automatic sampler mechanism for use with liquid chromatrographs.

The efficiency with which the sample is used is an important factor in the construction and operation of autosampler mechanisms. There are two parameters which contribute to the efficiency. One of the parameters is the minimum amount of sample that must be in the sample tube to enable the sample to be removed for use in the liquid chromatograph. A second parameter which contributes to the efficiency is the amount of sample that must be removed from a vial containing the sample in order to be able to inject the sample into the liquid chromatograph.

A number of mechanisms have been used in the prior art for withdrawing samples from sample vials. These prior art mechanisms include syringe transport mechanisms and purge mechanisms.

In the prior art syringe transport mechanisms the syringe is physically inserted into the sample vial, a portion of the sample is drawn into the syringe, and the syringe is then removed from the sample vial and mechanically moved and connected to another sample injection mechanism.

Prior art purge mechanisms operated by purging a sample loop. Purge mechanisms used in the prior art were uncontrolled, that is, gas pressurization or suction alone was relied on to move the sample from the vial into loop; and such purge mechanisms were usually used with a complete loop fill only.

The prior art syringe transport offers the benefit of low waste level, i.e. only the amount of the sample to be injected is removed from the vial by the syringe. As a result, multi samples may be taken and rejected to waste to minimize cross contamination before one sample is injected into the chromatograph, and the syringe transport is still a relatively efficient mechanism. However, the prior syringe transport mechanisms have a number of problems, including problems of mechanical alignment and high pressure seals.

The purge mechanisms which use gas pressurization or suction to remove samples from the vial require flexible lines in order to accomodate the movement of the needle into the sample vial. This has made it necessary to remove relatively large volumes, in excess of 30 milliliters of sample in order to purge the system. Also, only fixed volumes could be injected using prior art purge mechanisms of this type.

Primary objects of the present invention include minimizing the dead volume between the sample point and the injection point, allowing for variable volume injection, minimizing mechanical alignment problems, controlling the volume removed, and providing for efficient flush and cleanout of the system.

SUMMARY OF THE PRESENT INVENTION

The autosampler mechanism of the present invention has a fixed, non-moving needle at a sampling station. To take the sample from a sample vial, the sample vial is lifted from a tray of the sampling station and is moved axially relative to the needle to cause the needle to pierce the septum of the vial. The needle then enters the sample with continued axial movement of the vial.

The needle has an inner, sample needle and an outer, gas pressurization needle. The outer needle has a larger diameter than the sample needle so as to leave a space between the needles for the flow of pressurized gas into the sample vial. The sample is withdrawn through the sample needle under the control of the syringe connected to the sample needle. The combination of the gas pressurization within the vial and the positive displacement of the syringe insures movement of the sample and accurate control of the volume of the sample removed independent of the viscosity of the sample. Because the amount of sample withdrawn is controlled, less than a full loop of sample can be used.

A flush solvent mechanism is associated with the syringe so that the solvent in the syringe is always the flush solvent and never the sample. This has the advantqage of minimizing the possibility of contamination.

A flush solvent mechanism is associated with the syringe so that the solvent in the syringe is always the flush solvent and never the sample. This has the advantage of minimizing the possibility of contamination.

A bar code reader is located at the sampling station to provide label identification of each sample taken. The sample vial at the sampling station is rotated as it is moved axially. The bar code reader makes a number of spaced apart helical reads on a bar code label attached to the vial as the vial is moved axially and rotated. The label rotates past the reader sensor several times on each reading operation before the needle pierces the capped septum. If proper readings are not obtained, the vial is moved away from the needle and the operation is started all over again. Because the angle of the helix is slight in comparison to the length of the bar codes on the label, a number of readings can be taken for each item of alphanumeric information on the bar code label. If there is a blemish at one spot on the label, subsequent readings can be taken at different levels to avoid the blemish.

The sample vials are conducted to and away from the sample station by a tray mechanism which includes a rotatable platter and four planetary trays carried by and rotatable on the main platter. A clutch and brake drive permits the entire tray assembly to be rotated as a unit and also permits rotation of the planetary trays relative to the main platter so that any sample vial can be positioned at the sample station in any desired sequence with respect to the other sample vials.

Autosampler apparatus and methods which incorporate the structures and techniques described above and which are effective to function as described above constitute specific objects of this invention.

Other and further objects of the present invention will be apparent from the following description and claims and are illustrated in the accompanying drawings which, by way of illustration, show preferred embodiments of the present invention and the principles thereof and what are now considered to be the best modes contemplated for applying these principles. Other embodiments of the invention embodying the same or equivalent principles may be used and structural changes may be made as desired by those skilled in the art without departing from the present invention and the purview of the appended claims.

BRIEF DESCRIPTION OF THE DRAWINGS

FIG. 2 shows a cross-section through the tower assembly at the sampling station.

FIG. 3 has been partly broken away to show details of the drive motor and main-drive belt for the main platter of the tray mechanism which holds the sample vials.

FIG. 4 is taken generally along the line and in the direction indicated by the arrows 4—4 in FIG. 3.

DESCRIPTION OF THE PREFERRED EMBODIMENTS

Figure 1:
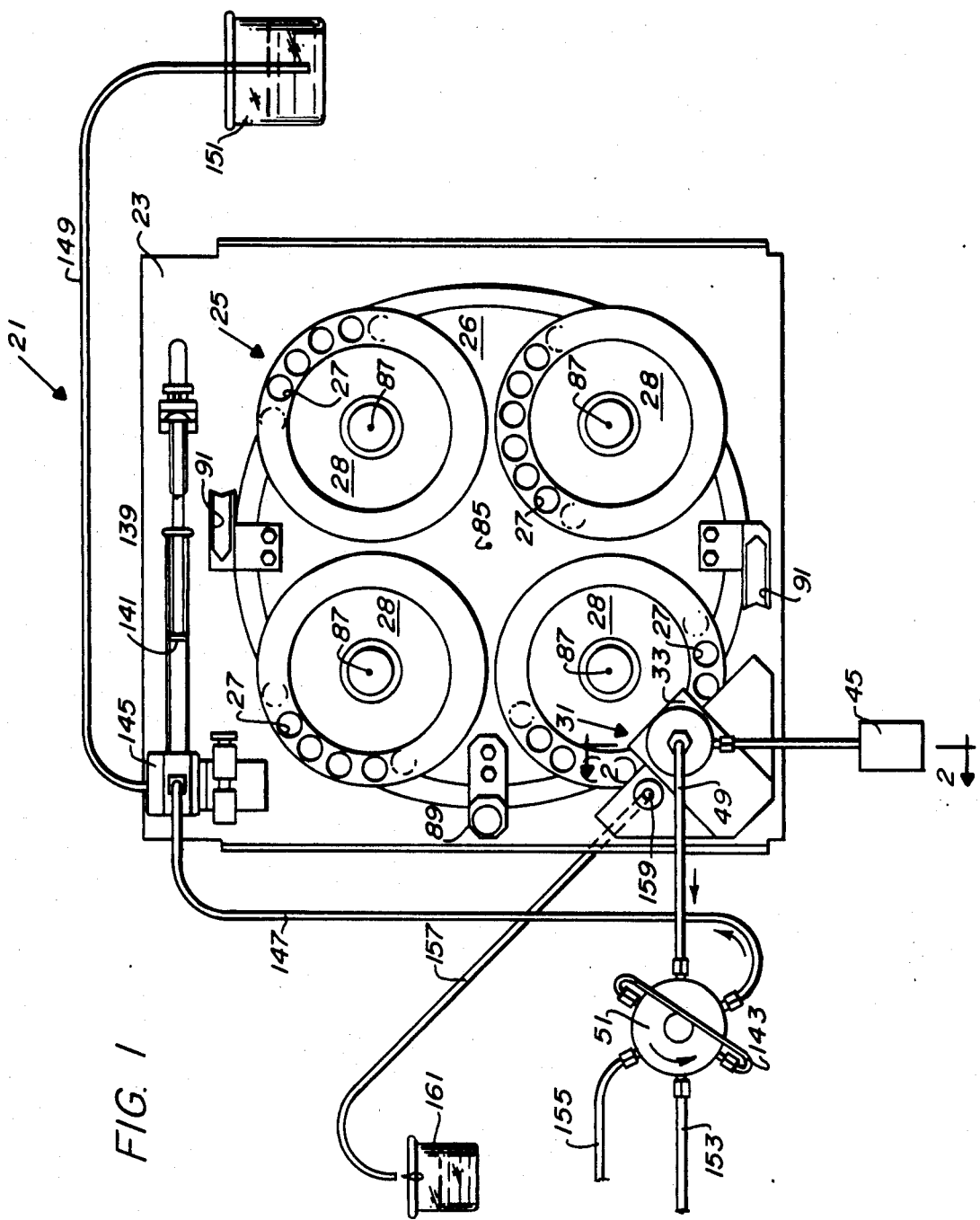
FIG. 1 is a top-plan view of an autosampler mechanism constructed in accordance with one embodiment of the present invention.

An autosampler mechanism constructed in accordance with one embodiment of the present invention is indicated generally by reference numeral 21 in FIG. 1.

The autosampler mechanism 21 comprises a frame 23.

Figure 6:
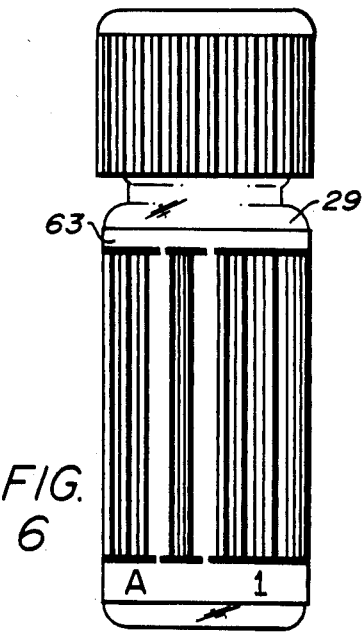
FIG. 6 is an elevation view of a sample vial used with the autosampler mechanism of the present invention.

A tray mechanism 25 is mounted for rotation in the frame 23. The tray mechanism 25 has a plurality of vial holder openings or slots 27 (see also FIG. 2) for holding sample vials like the vial 29 shown in FIG. 6.

The sample is taken from a vial 29 at a sampling station 31 (see FIG. 1).

A tower assembly 33 is mounted on the frame 23 at the sampling station 31.

Figure 2:
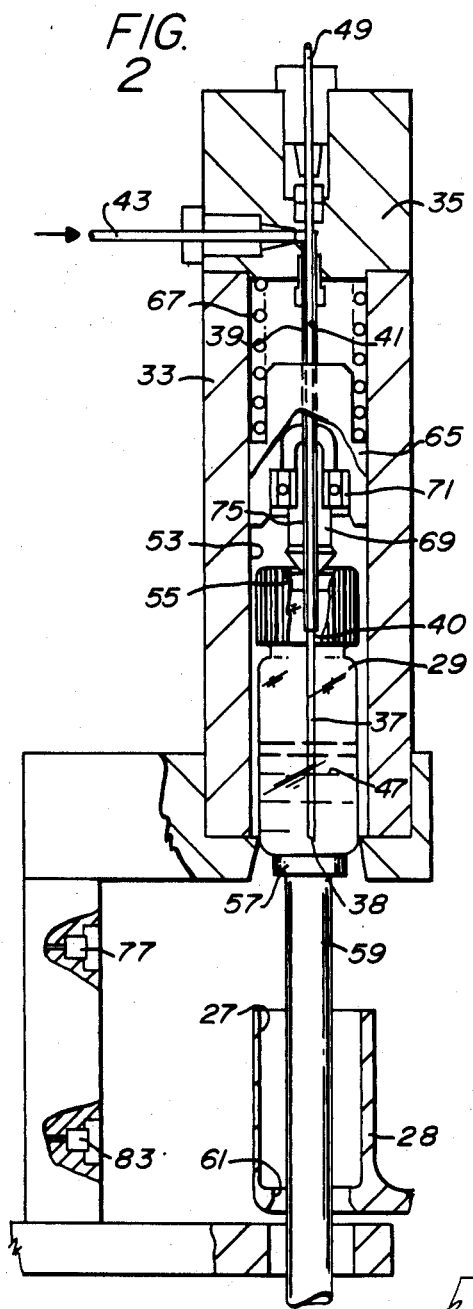
FIG. 2 is an elevation view taken along the line and in the direction indicated by the arrows 2—2 in FIG. 1.

As illustrated in FIG. 2, the tower assembly 53 has a headblock 35.

A needle assembly comprising an inner, sample needle 37 and an outer, pressurization needle 39 is mounted in a fixed position in the headblock 35. The outer needle 35 is concentric with the inner needle 37 and has an inner diameter larger than the outer diameter of the needle 37 so as to provide an annular passageway 41 between the two needles. Pressurized gas is supplied to this annular space 41 by a conduit 43 under the control of a control valve 45 (see FIG. 1).

The inner needle 37 is longer than the outer needle 39 so that the lower end 38 of the needle 37 extends downward beneath the surface of the liquid sample 47 while the lower end 40 of the outer needle 39 remains above the surface of the liquid sample 47 when the sample vial 29 has been lifted to the sampling position illustrated in FIG. 2.

A sample line 49 is connected to the upper end of the inner needle 37.

As will be described in detail below, the liquid sample is drawn up through the open lower end 38 of the inner needle 37 by the combination of the pressure exerted by the gas in the line 43 and the suction produced by a syringe 139 connected to the sample line 49. The sample in the line 49 is conducted to a six-port injector valve 51 which is a standard injector valve, such as a Valco or Rheodyne (model) valve.

As will also be described in greater detail below, the sample is injected from the injector valve 51 into a sample-using device, such as, for example, a liquid chromatograph.

With continued reference to FIG. 2, the tower assembly 33 has an inner bore 53 which is somewhat larger in diameter than the diameter of a sample vial 29 so as to permit the sample vial 29 to be lifted out of the opening 27 of the vial tray and moved upward within the bore 53 to the position illustrated in FIG. 2 (where both the inner needle 37 and the outer needle 33 have pierced the septum 55 in the cap of the vial and the lower end 38 of the sample needle has been located closely adjacent the bottom of the vial 29).

The sample vial 29 is lifted out of the tray opening 27 at the sampling station 31 by a lift mechanism which includes a rubber lift pad 57 engagable with the bottom end of the vial 29 and a vial lifting screw 59. The vial tray has an opening 61 below each vial holding slot 27 so that the rubber lift pad 57 can engage the bottom end of the vial 29 and lift it out of the holder slot 27 and to the sampling position as illustrated in FIG. 2.

The vial lifting screw 59 is driven by a drive mechanism which moves the vial 29 longitudinally upward as illustrated in FIG. 2 and which also rotates the vial 29 as it is moved upwardly. The drive mechanism for the vial lifting screw is not illustrated in the drawings. It should be noted, however, that there is a substantial amount of rotational movement for each increment in longitudinal movement so that if a beam of light were directed onto the vial from a fixed location in the tower assembly 33 as the sample vial 29 is lifted by the vial lifting screw 59, the beam of light would trace a spiral or helical path on the outer, cylindrical surface of the vial 29, and the pitch or space between adjcent lines of the helical trace would be small. This has significance in connection with bar code readings that are taken from the bar code label attached to each sample vial 29. The bar code reading method of the present invention will be described in greater detail below.

To continue the description of the structure and operation of the tower assembly 33, a crosshead 65 is mounted for sliding movement upwardly and downwardly within the bore 53 and is biased in a downward direction by a vial return spring 67.

A vial cap stabilizer is mounted for rotation within the crosshead 65 by a bearing assembly 71. As illustrated in FIG. 2, the vial cap stabilizer 69 engages the septum 55 of the sample vial 29 as the vial lifting screw 59 lifts and rotates the vial 29.

The crosshead 65 has an opening 73, and the vial cap stabilizer 69 has an opening 75 which permits the parts 65 and 69 to move up and down with respect to the fixed needles 37 and 39.

An optical element 77 of a bar code reader is mounted in a side wall 79 of the frame 23 at the sampling station 31. The optical element 77 is spaced for enough away from the vial lifting screw 59 so that the optical element never contacts the bar code labels 63 which are read by the bar code reader. The optical element 77 is aligned with the axis of the vial lifting screw 59 and is positioned at a vertical location in the side wall 79 to enable the optical element 77 to read along the entire vertical height of the bar codes on the label as the sample vial is lifted and rotated out of the slot 27.

Figure 7:
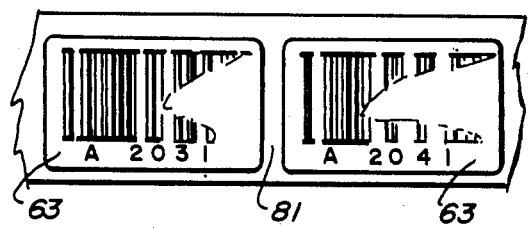
FIG. 7 is a plan view of a paper strip having peel of bar code labels for application to sample vials in accordance with the present invention.

As illustrated in FIG. 7 each label 63 contains alphanumeric information. The individual labels 63 are peel off labels which are carried on a backing strip 81. In the strip 81 illustrated in FIG. 7 the last number of the alphanumeric number at the bottom of the label is the number of the method to be run—in this case method 1. The three numbers preceding the last number are sample numbers, that is, sample numbers 200 and 201 as shown in FIG. 7.

In one particular embodiment of the invention ten different methods can be run, numbers 0 through 9, and there are ten different strips 81 having last numbers reading 0 through 9 to inidicate the 10 methods.

Using the labels illustrated in FIG. 7 the optical element 77 makes four separate reads (with each read occurring along a helical path and axially spaced from the other reads) to pick up the alphanumeric information from the bar code (as indicated in the lettering and numerals beneath the bar code portion of the label). Since only a small amount of axial, longitudinal movement of the sample vial 29 is required to enable one complete read to be made across the lateral extent of the bar code, readings can be repeated several times. Thus, if there is a blemish on the label, the same point does not have to read each time; and a reading can be repeated to obtain an accurate response if there is a blemish at some particular point in the label during the first read. Reads can also be made by rotation without longitudinal movement if desired.

Also, in the operation of the bar code reader of the present invention, the label is rotated past the optical element 77 several times on each reading operation before the vial 29 is lifted to a point where it can be pierced by the lower end 38 of the inner needle 37. If the bar code reader does not work right, the sample vial 29 is lowered and the lifting operation is started again before any piercing of the septum 55 occurs.

As also illustrated in FIG. 2, a tray identification sensor optical element 83 is mounted in the sidewall 79 for sensing a location marking on each of the planetary vial trays 28 to provide slot identification, as will be described in greater detail below.

As can be seen from FIG. 1, the tray mechanism 25 is a compact mechanism which enables a large number of sample vials to be retained in a relatively small area while permitting any sample vial in the tray mechanism to be conveyed to the sample station 31 in any sequence with respect to the other sample vials.

The tray mechanism comprises a main, circular platter and four planetary trays 28. The platter 26 is mounted for rotation about a central axis 85 (see FIG. 4 and FIG. 1). Each of the planetary trays 28 is mounted for rotation with respect with the main platter 26 about an axis 87. All of the axes 87 are located at the same distance from the axis 85, and all of the planetary trays 28 are identical in construction to one another.

The tray mechanism 25 may be rotated as a unit (without any relative rotation between the planetary trays 28 and the main platter 26) or the planetary trays 28 may be rotated while the main platter 26 is held stationary in order to bring a sample at any particular slot location 27 to the sampling position at the sampling station 31.

A single vial holder 89 is mounted on the main circular platter 26 to simplify operation when only a single sample is to be taken.

One or more flush funnels 91 are also mounted on the main platter 26 for use in a flushing operation to be dsecribed in more detail below.

Figure 3:
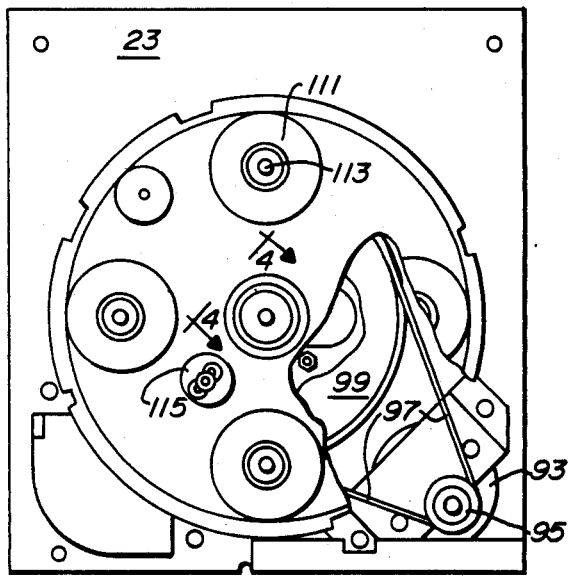
FIG. 3 is a bottom-plan view of the autosampler mechanism shown in FIG. 1.
Figure 4:
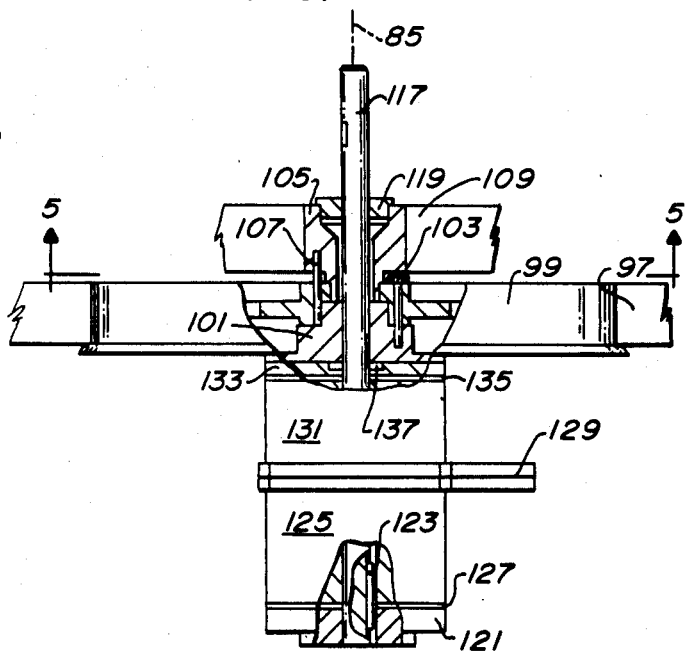
FIG. 4 is an elevation view, partly broken away to show details of construction, of the clutch and brake drive for the vial tray mechanism.
Figure 5:
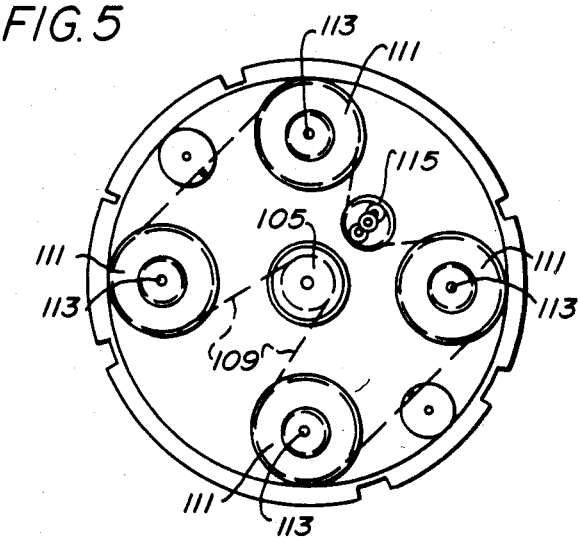
FIG. 5 is a bottom-plan view showing the drive pulley and belt arrangement for rotating the planetary trays relative to the main platter of the tray mechanism.

Details of the drive for the tray mechanism 25 are illustrated in FIGS. 3-5.

As illustrated in FIG. 3 a motor 93 is mounted in the frame 23 to drive a main drive pulley 95 and a main drive belt 97.

With reference to both FIGS. 3 and 4, the drive belt 97 drives a pulley 99 which is attached to a hub 101 by cap screws 103.

A pulley 105 is locked to the pulley 99 by dowel pins 107.

The pulley 105 serves as the drive pulley for a drive belt 109 which is trained over individual pulleys 111 connected to drive shafts 113 of the planetary trays 28.

An idler pulley 115 (see FIG. 5) is adjustable to maintain the proper tension on the belt 109.

The drive shaft 117 (see FIG. 4) is mounted for rotation within the pulley 105 by a bearing 119.

Looking at the lowest part of FIG. 4, the shaft 117 is keyed for rotation with a brake pad 121 by a key 123.

The brake pad 121 is rotatable with respect to a brake electromagnet 125 by means of a spacer 127 when the electromagnet is not energized. When the brake electromagnet 125 is energized, the brake pad 121 and the shaft 117 are held against rotation because the electromagnet 125 is connected to the frame 23 by a mounting flange 129.

A clutch electromagnet 131 is also mounted on the flange 129.

A disk 133 is connected to the shaft 117 and thus rotates with the brake pad 121. The disk 133 is separated from the clutch electromagnet 131 by a floating spacer washer 135.

A washer 137 permits rotation of the disk 133 with respect to the hub 101 when the clutch electromagnet 131 is not energized. When the clutch electromagnet 131 is energized, the disk 133 is locked to the hub 101.

There are three modes of operation produced by selective energization of the clutch electromagnet 131 and brake electromagnet 125.

In a first mode of operation both the clutch electromagnet 131 and the brake electromagnet 125 are energized. This produces a holding device which retains the tray mechanism 25 fixed in position. In this mode of operation power to the drive motor 93 can be shut off. The tray mechanism 25 is not dependent on the drive belt 97 for holding the tray mechanism fixed.

In a second mode of operation the brake electromagnet 125 is de-energized and disengaged and the clutch electromagnet 131 is energized to engage the clutch. In this mode of operation the entire tray mechanism 25 is rotated as a unit while the individual planetary trays 28 are held against rotation with respect to the platter 26.

In the third mode of operation the brake electromagnet 125 is energized to engage the brake, and the clutch electromagnet 131 is de-energized to disengage the clutch. In this mode of operation the planetary trays 28 are rotated with respect to the main platter 26 while the main platter 26 is held against rotation.

As noted above, samples can be identified by slot location in the tray mechanism. Each planetary tray has an orientation spot located on its outer periphery for reading by the sensor 83, and there are identifying elements located under each slot 27 in each of the planetary trays 28 for identifying the location of a particular slot in a particular planetary tray.

With reference now to FIG. 1, the sampling mechanism 21 includes the syringe 139 mounted on the frame 23 for withdrawing a sample from the vial 29 at the sampling station.

Figure 8:
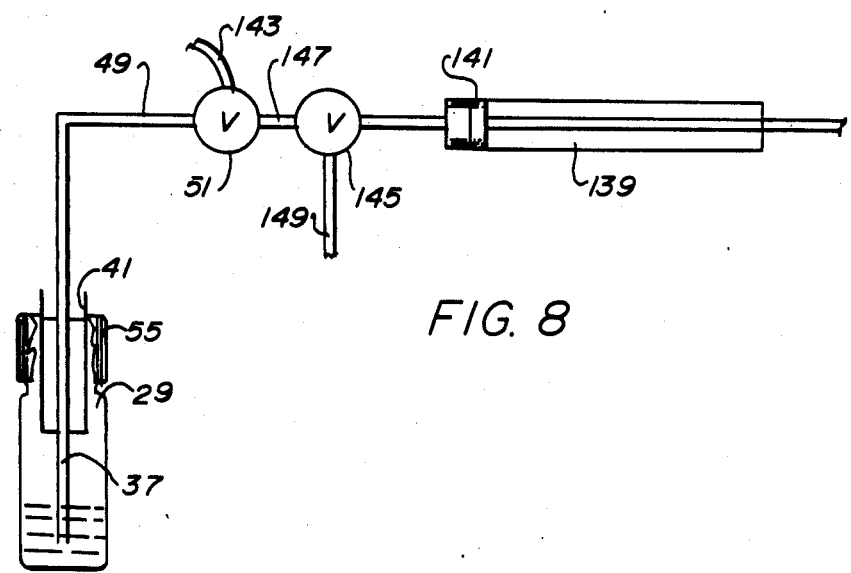
FIG. 8 is a diagramatic view showing how a positive displacement syringe is associated with a pressurized needle assembly for withdrawing a sample from a vial at the sampling station.

The way in which the syringe 139 acts to withdraw a sample from the vial 29 is illustrated in somewhat simplified, diagramatic form in FIG. 8.

With reference to both FIG. 1 and FIG. 8, the syringe 139 includes a plunger 141 which is retractable to withdrawn a sample from the vial at the sampling station into a loop 143 and which moves forward as the sample is injected from the loop 143 into the sample using apparatus, such as, for example, a liquid chromatograph.

With reference to both FIGS. 8 and 1, a three-way solvent valve 145 is connected in a solvent line 147 which extends between the injector valve 51 and the syringe 139. The other connection to the three-way solvent valve 145 is a line 149 connected to a flush solvent reservoir 151.

A pump in line 153 in connected to the injector valve 51 and a pump out line 155 is also connected to the injector valve 51.

As illustrated in FIG. 1, a flush drain tube 157 has an open end 159 located in the tower assembly 33 and another end associated with a flush waste container 161. The end 159 is positioned in the tower assembly so that when a sample is flushed from the sample line 49 by the action of the flush valve 145, the flushed waste is directed by a flush funnel 91 (located underneath the end 38 of the sample needle) into the open end 159, and the waste is then carried through the drain tube 157 to the container 161.

As noted above in the description, gas pressure fed through the gas pressure line 43 and out the lower end 40 of the gas pressurization needle 39 pressurizes the sample 47 within the vial to insure that the suction exerted by the retraction of the plunger 141 of the syringe 139 (an exerted through the solvent line 147, the injector valve 51 and the sample line 49) withdraws a positive, controlled amount of the sample as determined by the stroke of the plunger 141, regardless of the viscocity of the sample. The action of the gas pressure in line 43 also minimizes a tendency of the sample 47 to vaporize during the suction stroke, such as might otherwise happen with low vapor pressure samples.

The present invention always maintains the conduit 147 full of solvent for minimizing the possibility of contamination.

As can be seen by looking at FIG. 8, the conduits 147 and 49 act as a single interconnected conduit during the suction stroke.

The way in which the conduit 147 is always maintained full of solvent also permits operation with only partial filling of the loop 143 with the sample, as may be desired in cases where only small amounts of sample are available or where the sample might be expensive.

The actual injection is done by the high pressure exerted by the pump in line 153. During the injection step, the injector valve 51 blocks any return flow back to the sample line 49.

While we have illustrated and described the preferred embodiments of our invention, it is to be understood that these are capable of variation and modification, and we therefore do not wish to be limited to the precise details set forth, but desire to avail ourselves of such changes and alterations as fall within the purview of the following claims.

We claim:

1. A bar code reading apparatus for reading bar code labels on sample vials, said bar code reader apparatus comprising, a plurality of sample vials, each sample vial comprising a generally cylindrically shaped container, a bar code label attached to the outer cylindrical surface of the vial with the bar codes extending generally parallel to the cylindrical axis of the vial, sensor means mounted at a fixed location for reading the bar codes on the label, and vial transport means for rotating the sample vial with attached bar code label in front of the sensor means, and wherein the vial transport means also move the vial longitudinally with respect to the sensor means so that the sensor means read a helical path on the bar code label.

2. The invention defined in claim 1 wherein the vial transport means produce a longitudinal movement which is relatively small during each rotation of the vial so that the pitch of the helical path is small and the sensor means can make multiple, spaced reads within the length of the bars on the bar code label and can also make repeat readings at different locations on the bar codes of the bar code in the event there is a blemish at any point or points in the label.

* * * * *